United States Patent
Haviv et al.

(10) Patent No.: US 7,432,245 B2
(45) Date of Patent: Oct. 7, 2008

(54) PHARMACEUTICAL FORMULATION COMPRISING A PEPTIDE ANGIOGENESIS INHIBITOR

(75) Inventors: Fortuna Haviv, Deerfield, IL (US);
Bryan K. Erickson, Pleasant Prairie, WI (US); Jack Henkin, Highland Park, IL (US); Luk C. Li, Lake Forest, IL (US); Fanfeng Ma, Vernon Hills, IL (US); Friedrich W. Richter, Lake Bluff, IL (US); Yi Shi, Libertyville, IL (US); Jingfeng Song, Waukegan, IL (US); Siriporn Toongsuwan, Gurnee, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 533 days.

(21) Appl. No.: 10/456,831

(22) Filed: Jun. 6, 2003

(65) Prior Publication Data

US 2003/0229022 A1    Dec. 11, 2003

Related U.S. Application Data

(60) Provisional application No. 60/386,817, filed on Jun. 7, 2002.

(51) Int. Cl.
*A61K 38/08*  (2006.01)
*C07K 7/06*  (2006.01)

(52) U.S. Cl. ........................................ 514/16; 530/328
(58) Field of Classification Search ................... 514/16; 530/328
See application file for complete search history.

(56) References Cited

U.S. PATENT DOCUMENTS

| | | | |
|---|---|---|---|
| 4,938,763 | A | 7/1990 | Dunn et al. |
| 5,780,044 | A | 7/1998 | Yewey et al. |
| 5,945,115 | A | 8/1999 | Dunn et al. |
| 5,990,194 | A | 11/1999 | Dunn et al. |
| 6,130,200 | A | 10/2000 | Brodbeck et al. |
| 6,143,314 | A | 11/2000 | Chandrashekar et al. |
| 6,261,583 | B1 | 7/2001 | Dunn et al. |

FOREIGN PATENT DOCUMENTS

| | | |
|---|---|---|
| EP | 0 949 905 | 7/2001 |
| WO | 92/07555 | 5/1992 |
| WO | 99/61476 | 12/1999 |
| WO | 00/74650 | 12/2000 |
| WO | 01/35929 | 5/2001 |

*Primary Examiner*—Jon P Weber
*Assistant Examiner*—Rosanne Kosson
(74) *Attorney, Agent, or Firm*—B. Gregory Donner

(57) ABSTRACT

Parenteral formulations of peptides which are useful for sustained release are disclosed. Also disclosed are methods of preparation for the formulations.

16 Claims, 11 Drawing Sheets

PHARMACEUTICAL FORMULATION COMPRISING A PEPTIDE ANGIOGENESIS INHIBITOR

CROSS-REFERENCE TO RELATED APPLICATIONS

This application claims priority to U.S. Provisional Patent Application Ser. No. 60/386,817, filed on Jun. 7, 2002, which is hereby incorporated by reference.

TECHNICAL FIELD

The present invention relates to parenteral formulations of peptides. These formulations are useful for sustained release of the peptides. Methods for the preparation of the formulations and methods for their use are also disclosed.

BACKGROUND OF THE INVENTION

The peptides of the present invention have been shown to inhibit angiogenesis, the fundamental process by which new blood vessels are formed that is essential to a variety of normal body activities (such as reproduction, development, and wound repair). Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition.

In many instances, the therapeutic effectiveness of a pharmaceutically active peptide depends on its continued presence in vivo over prolonged time periods. A sustained release formulation or sustained drug delivery is desirable to avoid the need for repeated administrations. Formulations which provide sustained release have been the subject of intensive research (see, for example, WO0135929; WO0074650; WO9207555; EP0949905; and U.S. Pat. Nos. 5,990,194; 6,143,314; 5,780,044; 5,945,115; 6,261,583; 6,130,200; and 5,783,205). Different approaches are often taken when formulating pharmaceutically active peptides. For example, Lupron® and Eligard®, which both contain the peptide leuprolide acetate, use different formulations for drug delivery.

Peptides useful in the treatment of conditions caused or exacerbated by angiogenesis are known (see, for example, WO99/61476). We have discovered that the sustained release properties of the aforementioned prior art formulations cannot be predictably applied to these antiangiogenic compounds. The irregularity exhibited when the known formulations are applied to pharmaceutically active peptides poses an impediment in the development of reliable sustained release formulations. Therefore, additional sustained delivery formulations for administering pharmaceutically active antiangiogenic drugs, particularly peptides, are still needed.

SUMMARY OF THE INVENTION

In its principle embodiment the present invention provides a pharmaceutical composition comprising:

(a) a therapeutically effective amount of a compound of formula (I)

$R^1$-Xaa$_1$-Xaa$_2$-Xaa$_3$-Xaa$_4$-Xaa$_5$-Xaa$_6$-Ile-Arg-Pro-Xaa$_{10}$(SEQ ID NO:1); (I), or a therapeutically acceptable salt thereof, wherein
$R^1$ is $CH_3$—C(O)—;
Xaa$_1$ is absent or sarcosyl;
Xaa$_2$ is absent or glycyl;
Xaa$_3$ is absent or selected from the group consisting of glutaminyl and valyl;
Xaa$_4$ is absent or selected from the group consisting of D-alloisoleucyl and D-isoleucyl;
Xaa$_5$ is selected from the group consisting of seryl and threonyl;
Xaa$_6$ is selected from the group consisting of glutaminyl, norvalyl, and seryl; and
Xaa$_{10}$ is selected from the group consisting of —NHCH$_2$CH$_3$ and D-alanylethylamide; provided that when Xaa$_4$ is D-alloisoleucyl, Xaa$_1$ is absent;
(b) poly(lactide-co-glycolide); and
(c) an organic solvent.

In a preferred embodiment the compound of formula (I) is selected from the group consisting of
N-Ac-DalloIle-Thr-Ser-Ile-Arg-ProNHCH$_2$CH$_3$;
N-Ac-Thr-Gln-Ile-Arg-ProNHCH$_2$CH$_3$ (SEQ ID NO:2); and
N-Ac-Gly-Gln-DIle-Thr-Nva-Ile-Arg-Pro-DAlaNH$_2$.

More preferably, the compound of formula (I) is selected from the group consisting of
N-Ac-Sar-Gly-Val-DIle-Thr-Nva-Ile-Arg-ProNHCH$_2$CH$_3$;
N-Ac-Sar-Gly-Val-DIle-Thr-Gln-Ile-Arg-ProNHCH$_2$CH$_3$;
N-Ac-DalloIle-Ser-Ser-Ile-Arg-ProNHCH$_2$CH$_3$; and
N-Ac-Gly-Val-DalloIle-Ser-Gln-Ile-Arg-ProNHCH$_2$CH$_3$.

In another preferred embodiment the therapeutically acceptable salt is selected from the group consisting of acetate, pivalate, valproate, and octanoate.

In another preferred embodiment the pharmaceutical composition comprises between about 1% and about 15% (w/w) of the compound of formula (I), or a therapeutically acceptable salt thereof. More preferably, the pharmaceutical composition comprises between about 3% and about 6% (w/w) of the compound of formula (I), or a therapeutically acceptable salt thereof.

In another preferred embodiment the pharmaceutical composition comprises between about 25% and about 45% (w/w) poly(lactide-co-glycolide), more preferably about 35%. In another preferred embodiment the poly(lactide-co-glycolide) has a weight of between about 6 and about 60 KD, more preferably between about 13 and about 24 KD.

In another preferred embodiment the organic solvent of the pharmaceutical composition is N-methyl-2-pyrrolidinone. In another preferred embodiment the organic solvent is triacetin. A particularly preferred organic solvent is a mixture of N-methyl-2-pyrrolidinone and triacetin. Preferably, the N-methyl-2-pyrrolidinone and the triacetin are in a weight ratio of from about 1:2 to about 6:1. More preferably, the N-methyl-2-pyrrolidinone and the triacetin are in a weight ratio of about 2:1 or about 1:1.

In another embodiment the present invention provides a pharmaceutical composition comprising:

(a) about 3% to about 5% (w/w) of the compound of formula (Ia)

N-Ac-Sar-Gly-Val-DIle-Thr-Nva-Ile-Arg-ProNHCH$_2$CH$_3$ (Ia), or a therapeutically acceptable salt thereof;
(b) about 35% (w/w) poly(lactide-co-glycolide); and
(c) about a 2:1 (w/w) mixture of N-methylpyrrolidinone and triacetin.

In a preferred embodiment the therapeutically acceptable salt is selected from the group consisting of acetate, pivalate, valproate, and octanoate.

In another embodiment the present invention provides a pharmaceutical composition comprising:
(a) about 3% (w/w) of the compound of formula (Ib)

N-Ac-Sar-Gly-Val-DIle-Thr-Gln-Ile-Arg-ProNHCH₂CH₃     (Ib), or a therapeutically acceptable salt thereof;
(b) about 35% (w/w) poly(lactide-co-glycolide); and
(c) about a 1:1 (w/w) mixture of N-methylpyrrolidinone and triacetin.

In a preferred embodiment the therapeutically acceptable salt is selected from the group consisting of acetate, pivalate, valproate, and octanoate.

In another embodiment the present invention provides a pharmaceutical composition comprising:
(a) about 6% (w/w) of the compound of formula (Ib)

N-Ac-Sar-Gly-Val-DIle-Thr-Gln-Ile-Arg-ProNHCH₂CH₃     (Ib), or a therapeutically acceptable salt thereof;
(b) about 33% (w/w) poly(lactide-co-glycolide); and
(c) about a 2:1 (w/w) mixture of N-methylpyrrolidinone and triacetin.

In a preferred embodiment the therapeutically acceptable salt is selected from the group consisting of acetate, pivalate, valproate, and octanoate.

In another embodiment the present invention provides a pharmaceutical composition comprising:
(a) about 3% (w/w) of the compound of formula (Ic)

N-Ac-DalloIle-Ser-Ser-Ile-Arg-ProNHCH₂CH₃     (Ic), or a therapeutically acceptable salt thereof;
(b) about 34% (w/w) poly(lactide-co-glycolide); and
(c) about a 2:1 (w/w) mixture of N-methylpyrrolidinone and triacetin.

In a preferred embodiment the therapeutically acceptable salt is selected from the group consisting of acetate, pivalate, valproate, and octanoate.

In another embodiment the present invention provides a pharmaceutical composition comprising:
(a) about 3% (w/w) of the compound of formula (Id)

N-Ac-Gly-Val-DalloIle-Ser-Gln-Ile-Arg-ProNHCH₂CH₃     (Id), or a therapeutically acceptable salt thereof;
(b) about 34% (w/w) poly(lactide-co-glycolide); and
(c) about a 2:1 (w/w) mixture of N-methylpyrrolidinone and triacetin.

In a preferred embodiment the therapeutically acceptable salt is selected from the group consisting of acetate, pivalate, valproate, and octanoate.

In another embodiment the present invention provides a method for preparing a pharmaceutical composition comprising:
(a) combining between about 25% and about 45% (w/w) poly(lactide-co-glycolide) and about 1% to about 15% (w/w) of a compound of formula (I), or a therapeutically acceptable salt thereof, in an organic solvent; and
(b) stirring the product of step (a).

In another embodiment the present invention provides a method for preparing a pharmaceutical composition comprising:
(a) dissolving between about 25% and about 45% (w/w) poly(lactide-co-glycolide) in an organic solvent selected from the group consisting of N-methyl-2-pyrrolidinone, triacetin, 2-pyrrolidinone, and mixtures thereof;
(b) treating the product of step (a) with about 2% to about 10% (w/w) of a compound of formula (I), or a therapeutically acceptable salt thereof; and
(c) stirring the product of step (b).

In a preferred embodiment the compound of formula (I) is selected from the group consisting of
N-Ac-DalloIle-Thr-Ser-Ile-Arg-ProNHCH₂CH₃;
N-Ac-Thr-Gln-Ile-Arg-ProNHCH₂CH₃ (SEQ ID NO:2); and
N-Ac-Gly-Gln-DIle-Thr-Nva-Ile-Arg-Pro-DAlaNH₂.

More preferably, the compound of formula (I) is selected from the group consisting of
N-Ac-Sar-Gly-Val-DIle-Thr-Nva-Ile-Arg-ProNHCH₂CH₃;
N-Ac-Sar-Gly-Val-DIle-Thr-Gln-Ile-Arg-ProNHCH₂CH₃;
N-Ac-DalloIle-Ser-Ser-Ile-Arg-ProNHCH₂CH₃; and
N-Ac-Gly-Val-DalloIle-Ser-Gln-Ile-Arg-ProNHCH₂CH₃.

In another preferred embodiment the therapeutically acceptable salt is selected from the group consisting of acetate, pivalate, valproate, and octanoate.

In another preferred embodiment the pharmaceutical composition comprises between about 33% and about 35% (w/w) poly(lactide-co-glycolide). In another preferred embodiment the poly(lactide-co-glycolide) has a weight of between about 13 and about 24 KD.

In another preferred embodiment the organic solvent of the pharmaceutical composition is N-methyl-2-pyrrolidinone. In another preferred embodiment the organic solvent is triacetin. A particularly preferred organic solvent is a mixture of N-methyl-2-pyrrolidinone and triacetin. Preferably, the N-methyl-2-pyrrolidinone and the triacetin are in a weight ratio of from about 1:2 to about 6:1. More preferably, the N-methyl-2-pyrrolidinone and the triacetin are in a weight ratio of about 2:1 or in a weight ratio of about 1:1.

In another preferred embodiment step (c) is conducted at about 20° C. to about 25° C.

In another embodiment the present invention provides a method for preparing a pharmaceutical composition comprising:
(a) dissolving about 35% (w/w) 13 KD poly(lactide-co-glycolide) in about a 2:1 (w/w) mixture of N-methyl-2-pyrrolidinone and triacetin;
(b) treating the product of step (a) with about 3% to about 5% (w/w) of the compound of formula (Ia), or a therapeutically acceptable salt thereof; and
(c) stirring the product of step (b) at about 20° C. to about 25° C.

In a preferred embodiment the therapeutically acceptable salt is selected from the group consisting of acetate, pivalate, valproate, and octanoate.

In another embodiment the present invention provides a method for preparing a pharmaceutical composition comprising:
(a) dissolving about 35% (w/w) 13 KD poly(lactide-co-glycolide) in about a 1:1 (w/w) mixture of N-methyl-2-pyrrolidinone and triacetin;
(b) treating the product of step (a) with about 3% (w/w) of the compound of formula (Ib), or a therapeutically acceptable salt thereof; and
(c) stirring the product of step (b) at about 20° C. to about 25° C.

In a preferred embodiment the therapeutically acceptable salt is selected from the group consisting of acetate, pivalate, valproate, and octanoate.

In another embodiment the present invention provides a method for preparing a pharmaceutical composition comprising:

(a) dissolving about 33% (w/w) 13 KD poly(lactide-co-glycolide) in about a 2:1 (w/w) mixture of N-methyl-2-pyrrolidinone and triacetin;

(b) treating the product of step (a) with about 6% (w/w) of the compound of formula (Ib), or a therapeutically acceptable salt thereof; and (c) stirring the product of step (b) at about 20° C. to about 25° C.

In a preferred embodiment the therapeutically acceptable salt is selected from the group consisting of acetate, pivalate, valproate, and octanoate.

In another embodiment the present invention provides a method for preparing a pharmaceutical composition comprising:

(a) dissolving about 34% (w/w) 13 KD poly(lactide-co-glycolide) in about a 2:1 (w/w) mixture of N-methyl-2-pyrrolidinone and triacetin;

(b) treating the product of step (a) with about 3% (w/w) of the compound of formula (Ic), or a therapeutically acceptable salt thereof; and (c) stirring the product of step (b) at about 20° C. to about 25° C.

In a preferred embodiment the therapeutically acceptable salt is selected from the group consisting of acetate, pivalate, valproate, and octanoate.

In another embodiment the present invention provides a method for preparing a pharmaceutical composition comprising:

(a) dissolving about 34% (w/w) 13 KD poly(lactide-co-glycolide) in about a 2:1 (w/w) mixture of N-methyl-2-pyrrolidinone and triacetin;

(b) treating the product of step (a) with about 3% (w/w) of the compound of formula (Id), or a therapeutically acceptable salt thereof; and (c) stirring the product of step (b) at about 20° C. to about 25° C.

In a preferred embodiment the therapeutically acceptable salt is selected from the group consisting of acetate, pivalate, valproate, and octanoate.

In another embodiment the present invention provides a method for providing sustained delivery of a peptide comprising administering to a subject a pharmaceutical composition comprising:

(a) about 1% to about 15% (w/w) of a compound of formula (I)

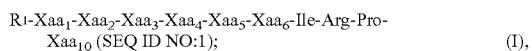

$R_1$-$Xaa_1$-$Xaa_2$-$Xaa_3$-$Xaa_4$-$Xaa_5$-$Xaa_6$-Ile-Arg-Pro-$Xaa_{10}$ (SEQ ID NO:1);    (I), or a therapeutically acceptable salt thereof, wherein $R^1$ is $CH_3$—C(O)—;

$Xaa_1$ is absent or sarcosyl;

$Xaa_2$ is absent or glycyl;

$Xaa_3$ is absent or selected from the group consisting of glutaminyl and valyl;

$Xaa_4$ is absent or selected from the group consisting of D-alloisoleucyl and D-isoleucyl;

$Xaa_5$ is selected from the group consisting of seryl and threonyl;

$Xaa_6$ is selected from the group, consisting of glutaminyl, norvalyl, and seryl; and $Xaa_{10}$ is selected from the group consisting of —NHCH$_2$CH$_3$ and D-alanylethylamide; provided that when $Xaa_4$ is D-alloisoleucyl, $Xaa_1$ is absent;

(b) about 25% to about 45% (w/w) poly(lactide-co-glycolide); and (c) an organic solvent selected from the group consisting of N-methyl-2-pyrrolidinone, triacetin, and mixtures thereof.

In a preferred embodiment the compound of formula (I) is selected from the group consisting of N-Ac-DalloIle-Thr-Ser-Ile-Arg-ProNHCH$_2$CH$_3$;

N-Ac-Thr-Gln-Ile-Arg-ProNHCH$_2$CH$_3$ (SEQ ID NO:2); and

N-Ac-Gly-Gln-DIle-Thr-Nva-Ile-Arg-Pro-DAlaNH$_2$.

More preferably the compound of formula (I) is selected from the group consisting of N-Ac-Sar-Gly-Val-DIle-Thr-Nva-Ile-Arg-ProNHCH$_2$CH$_3$;

N-Ac-Sar-Gly-Val-DIle-Thr-Gln-Ile-Arg-ProNHCH$_2$CH$_3$;

N-Ac-DalloIle-Ser-Ser-Ile-Arg-ProNHCH$_2$CH$_3$; and

N-Ac-Gly-Val-DalloIle-Ser-Gln-Ile-Arg-ProNHCH$_2$CH$_3$.

In another preferred embodiment the therapeutically acceptable salt is selected from the group consisting of acetate, pivalate, valproate, and octanoate.

DETAILED DESCRIPTION OF THE INVENTION

Figure 1:
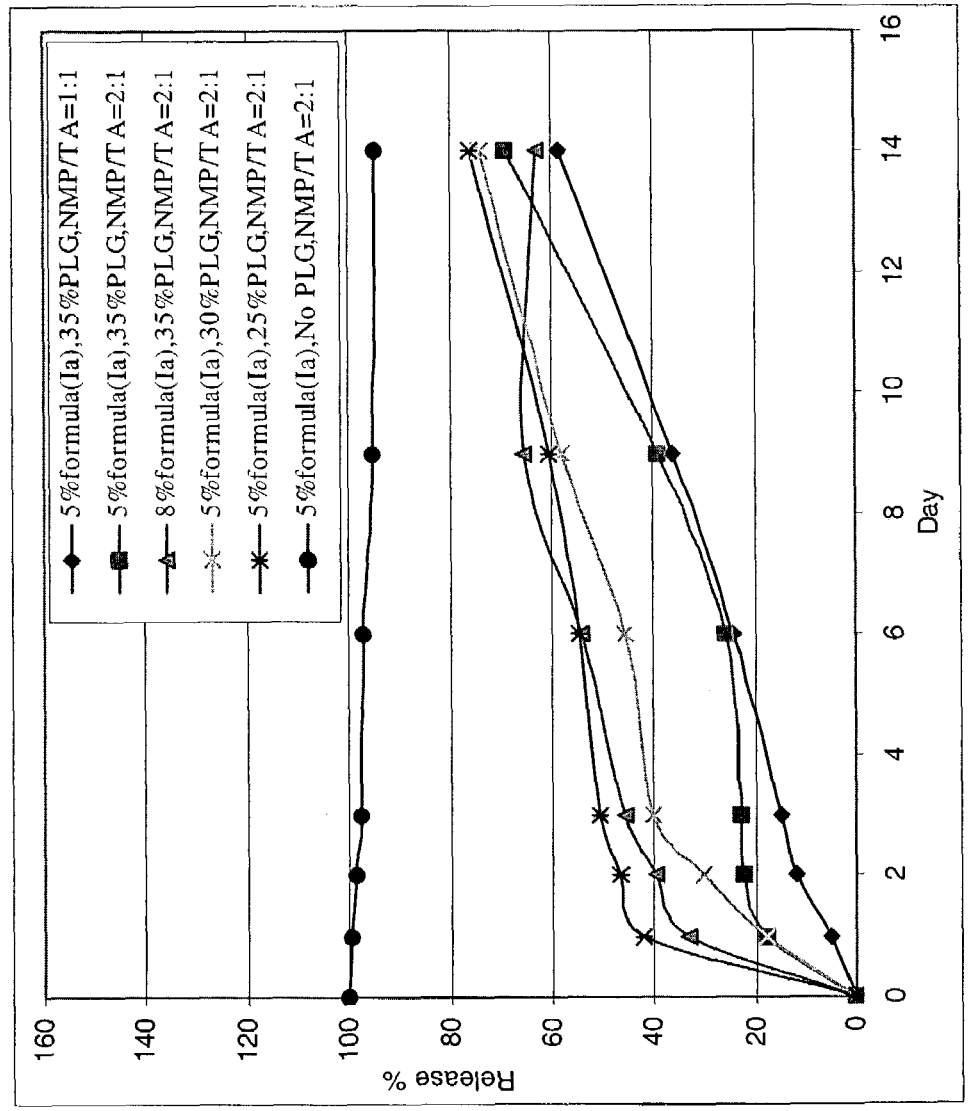
FIG. 1 illustrates the in vitro release profile of the compound of formula (Ia) from PLG (13 KD) gel formulations at 37° C.

The present invention relates to sustained release formulations of peptides that contain poly(lactide-co-glycolide) and organic solvents. These formulations have demonstrated in vitro as well as in vivo activity.

All publications, issued patents, and patent applications cited herein are hereby incorporated by reference.

As used in the present specification the following terms have the meanings indicated:

As used herein, the singular forms "a", "an", and "the" include plural reference unless the context clearly dictates otherwise.

The term "organic solvent," as used herein, refers to a single organic solvent or a mixture of two or more organic solvents that demonstrates no undue toxicity when added to the formulations of the present invention. Preferred organic solvents of the present invention include N-methyl-2-pyrrolidinone, 2-pyrrolidinone, triacetin, dimethylsulfoxide, benzyl benzoate, and mixtures thereof. Particularly preferred organic solvents of the present invention are N-methyl-2-pyrrolidinone, triacetin, and mixtures thereof.

The term "sustained delivery," as used herein, refers to the continual delivery of a pharmaceutical agent in vivo over a period of time following administration, preferably at least several days, a week, or several weeks. Sustained delivery of the agent can be demonstrated by, for example, the continued therapeutic effect of the agent over time. Alternatively, sustained delivery of the agent may be demonstrated by detecting the presence of the agent in vivo over time.

The pharmaceutical formulation contains a therapeutically effective amount of the compound of formula (I). The term "therapeutically effective amount," as used herein, refers to an amount effective, at dosages and for periods of time necessary, to achieve the desired result. A therapeutically effective amount of the compound of formula (I) may vary according to factors such as the disease state, age, and weight of the individual, and the ability of the compound (alone or in combination with one or more other drugs) to elicit a desired response in the individual. Dosage regimens may be adjusted to provide the optimum therapeutic response. A therapeutically effective amount is also one which any toxic or detrimental effects of the compound are outweighted by the therapeutically beneficial effects. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are only exemplary and are not intended to limit the scope or practice of the claimed composition.

The formulations described in the present invention are not suitable for the delivery of all peptides. We have shown that some peptides are not suitable for use in these formulations (i.e., they demonstrated no sustained release).

Many diseases (characterized as "angiogenic diseases") are driven by persistent unregulated angiogenesis. For example, ocular neovascularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., *Cancer Res.*, 46: 467-473 (1986), Folkman, J., *J. Natl. Cancer Inst.*, 82: 4-6 (1989)). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites, such as the liver, the lung, and the bones (Weidner, N., et. al., *N. Engl. J. Med.*, 324(1): 1-8 (1991)).

The compounds of the invention, including not limited to those specified in the examples, possess antiangiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungosides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents. The compounds of the invention can also be useful in the treatment of the aforementioned conditions by mechanisms other than the inhibition of angiogenesis.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including not limited to intestinal adhesions, Crohn's disease, atherosclerosis, scleroderma, and hypertrophic scars, i.e., keloids. Another use is as a birth control agent, by inhibiting ovulation and establishment of the placenta. The compounds of the invention are also useful in the treatment of diseases that have angiogenesis as a pathologic consequence such as cat scratch disease (*Rochele minutesalia quintosa*) and ulcers (*Helicobacter pylori*). The compounds of the invention are also useful to reduce bleeding by administration prior to surgery, especially for the treatment of resectable tumors.

Unless indicated otherwise by a "D" prefix, e.g., DAla or DIle, the stereochemistry of the α-carbon of the amino acids and aminoacyl residues in peptides described in this specification and the appended claims is the natural or "L" configuration.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature. To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Amino Acid Abbreviations

| Abbreviation | Definition |
| --- | --- |
| DAlaNH$_2$ | D-alanylamide |
| DalloIle | D-alloisoleucyl |
| N-Ac-DalloIle | N-acetyl-D-alloisoleucyl |
| Arg | arginyl |
| Gln | glutaminyl |
| Gly | glycyl |
| N-Ac-Gly | N-acetylglycyl |
| Ile | isoleucyl |
| DIle | D-isoleucyl |
| Nva | norvalyl |
| Pro | prolyl |
| ProNHCH$_2$CH$_3$ | prolyl-N-ethylamide |
| N-Ac-Sar | N-acetylsarcosyl |
| Ser | seryl |
| Thr | threonyl |
| N-Ac-Thr | N-acetylthreonyl |
| Val | valyl |

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects. The contents of all references, patents, and published patent applications cited throughout this application are hereby incorporated by reference.

Poly(lactide-co-glycolide) (PLG) was purchased from Alkermes, Inc. The ratio of the two monomers (PL:PG) was 50:50 or 75:25. N-Methyl-2-pyrrolinone (NMP) was purchased from ISP technologies and triacetin (glycerol triacetate) (TA) was purchased from Aldrich.

Dosing amounts for in vivo pharmacokinetic studies were varied as a method of determining the extent of sustained delivery that is achievable with these formulations.

Detection limits for measurable drug plasma concentrations differed between Example 8 and Example 14 due to the differences in the two peptides. The analytical methods used to determine the measurable drug plasma concentrations were the same in each example.

EXAMPLE 1

General Procedure for Preparation of Peptide Salts (a) Preparation of Ion Exchange Resin A BioRad AG 1-X2 anion exchange resin acetate form (150 g, catalog #140-1253, 0.6 meq/mL resin bed, 0.65 g/mL) was washed with 500 mL of dilute acetic acid (20 mL glacial acetic acid diluted to 500 mL in water) in a fritted glass suction filter. The resin was then washed with 1 L of HPLC grade water.

The desired organic acid (pivalic acid, valproic acid, or octanoic acid, 0.6 mol) was mixed with 2 L of HPLC grade water and treated with 0.9 equivalents of NaOH (22 g dissolved in 200 mL water) with stirring until the pH was neutral/slightly basic.

The above prepared resin was washed over a period of 45 minutes with the above prepared sodium salt of the desired organic acid. The resin was isolated by suction filtration and washed with 2 L of HPLC grade water. The resin was tested for conversion to the desired salt by stirring 2 g of resin with 2 mL of a 50 mM NaOH solution for 5 minutes, filtering the mixture, and lyophilizing the filtrate. The dried salt was analyzed by proton NMR to determine the percent conversion from acetate salt to desired salt.

(b) Preparation of Pivalate, Valproate, and Octanoate Salts of Peptides

The trifluoroacetate salt of the desired peptide (prepared by the procedures described in WO99/61476, PCT/US02/34811, and PCT/US02/34760) or the acetate salt of the desired peptide (prepared by the procedure described in Example 1c) in 20 mL of HPLC grade water was mixed with 10 g of the desired resin (prepared as described in Example 1a) and stirred for 15 minutes. A separate mixture of 40 g of resin in approximately 50 mL of water was poured onto a 3×20 cm column. The peptide-resin mixture was poured onto the column and the eluent was collected and recycled over the column for about 1 hour. The column was rinsed with 30 mL of water, pooled with the eluent, and lyophilized until dry to provide the desired salt of the desired peptide.

(c) Preparation of Acetate Salt of Peptides

The acetate salt can be prepared by the method described in Example 1b starting from the trifluoroacetate salt of the desired peptide (prepared by the procedures described in WO99/61476, PCT/US02/34811, and PCT/US02/34760) and commercially available acetate ion exchange resin (Bio-Rad AG 1-X2, acetate form) using 50 g of resin per 1.0 g of peptide.

EXAMPLE 2

Preparation of the Formulations of Compound of Formula (Ia) in PLG (13 KD) Gels (a) Formulation of 5% Acetate Salt of Formula (Ia) in 35% PLG Gel and NMP/TA (2:1) (Formulation I)

A mixture of NMP and TA (2:1, w/w) was prepared using 14.993 grams of TA and 30.022 grams of NMP. A portion of this solvent mixture (19.505 g) was stirred at room temperature with 10.515 g of PLG (13 KD, 50:50 polymer ratio). The resulting PLG (35%) solution was transparent and viscous. A portion of the PLG solution (12.026 g) was treated with the acetate salt of formula (Ia) (prepared as described in Example 1c). The mixture was stirred at room temperature until a clear gel formed. The resulting PLG formulation (formulation I) consisted of 4.98% acetate salt of formula (Ia), 33.28% PLG, 41.18% NMP and 20.56% TA (w/w), and could be stored under refrigeration.

(b) Formulation of 5% Acetate Salt of Formula (Ia) in 30% PLG Gel and NMP/TA (2:1) (Formulation II)

A 30% PLG solution in NMP/TA (2:1, w/w) was prepared from 9.018 g of the 35% PLG solution in NMP/TA made in Example 2a and 1.502 g of a 2:1 NMP/TA solvent mixture.

The resulting 30% PLG solution (9.008 g) was treated with 473.5 mg of the acetate salt of formula (Ia) (prepared as described in Example 1c) and stirred at room temperature resulting in a viscous liquid formulation (formulation II) which consisted of 4.99% acetate salt of formula (Ia), 28.53% PLG, 44.34% NMP and 22.14% TA (w/w).

(c) Formulation of 5% Acetate Salt of Formula (Ia) in 25% PLG Gel and NMP/TA (2:1) (Formulation III)

A mixture of 35% PLG solution in NMP/TA (2:1) made in Example 2a (7.4999 g) was diluted with 3.0140 g of a solvent mixture of NMP/TA (2:1). A portion of this solution (9.008 g) was stirred with 471.5 mg of the acetate salt of formula (Ia) (prepared as described in Example 1c) to provide a formulation (formulation III) which consisted of 5.01% acetate salt of formula (Ia), 23.73% PLG, 47.53% NMP and 23.73% TA (w/w).

(d) Formulation of 8% Acetate Salt of Formula (Ia) in 35% PLG Gel and NMP/TA (2:1)

A gel formulation of 8% acetate salt of formula (Ia) was prepared from 0.1747 g of the acetate salt of formula (Ia) (prepared as described in Example 1c) and 2.0638 g of 35% PLG solution in NMP/TA (2:1) (prepared as described in Example 2a). The mixture was stirred at room temperature to provide a liquid formulation which consisted of 7.80% acetate salt of formula (Ia), 32.25% PLG, 39.96% NMP and 19.99% TA (w/w).

(e) Formulation of 5% Acetate Salt of Formula (Ia) in PLG Gel and NMP/TA (1:1)

A mixture of 1.015 g of 35% PLG (13 KD, 50:50 polymer ratio) solution in NMP was mixed with 1.0016 g of 35% PLG (13 KD, 50:50 polymer ratio) solution in TA. A portion of the resulting solution (1.0046 g) was stirred with 50.8 mg of the acetate salt of formula (Ia) (prepared as described in Example 1c) at room temperature to provide a clear formulation which consisted of 4.81% acetate salt of formula (Ia), 33.26% PLG, 31.16% NMP and 30.77% TA (w/w).

EXAMPLE 3

Potency Determination

A sample of the acetate salt of formula (Ia) in PLG gel (prepared as described in Example 2) was dissolved in aqueous acetonitrile and further diluted with water. The precipitated polymer was subsequently removed by filtration through a membrane filter. The concentration of the compound of formula (Ia) in the filtrate was determined by HPLC. The acetate salt of formula (Ia) could be completely recovered from the PLG gel. There was no extensive degradation found by HPLC for any of the salts described in Example 2.

EXAMPLE 4

In Vitro Release of Acetate Salt of Formula (Ia) from PLG Gels

The samples of gel formulations of the acetate salt of formula (Ia) in PLG and NMP/TA were immersed in 5 mM PBS buffer (pH 7.4) and incubated at 37° C. At a predetermined time, 1 mL of the dissolution medium was withdrawn from the dissolution container, filtered, and assayed for the concentration of the acetate salt of formula (Ia) by HPLC. Fresh PBS buffer (1 mL) was added to replace the withdrawn medium.

As shown in FIG. 1, a solution of 5% of the acetate salt of formula (I) in 2:1 NMP/TA showed no sustained release. Alternatively, PLG gels containing 5% or 8% of the acetate salt of formula (I); 25%, 30% or 35% PLG; and NMP/TA in either a 2:1 or 1:1 ratio showed a more gradual release.

EXAMPLE 5

Pharmacokinetic Studies of the Acetate Salt of Formula (Ia) in PLG Gels

In vivo pharmacokinetic studies of the acetate salt of formula (Ia) in PLG gels were performed using dogs. Five groups of dogs were tested by subcutaneous injection. Three groups were given subcutaneous injections of the three gel formulations: formulations I, II, and III from Example 1. Each of the formulations was administered at a dose of 50 mg/dog. One control group was given a subcutaneous injection of the acetate salt of formula (I) in 5% dextrose in water (D5W) at a dose of 50 mg/dog and another control group was administrated placebos consisting of 30% PLG in a solvent mixture of NMP and TA (2:1). Nine blood samples were taken from the dogs during the first 24 hours after dosing, followed by daily sampling for 14 days. No irritation was seen at the injection site in any of the dogs that were given the PLG gels.

Figure 2:
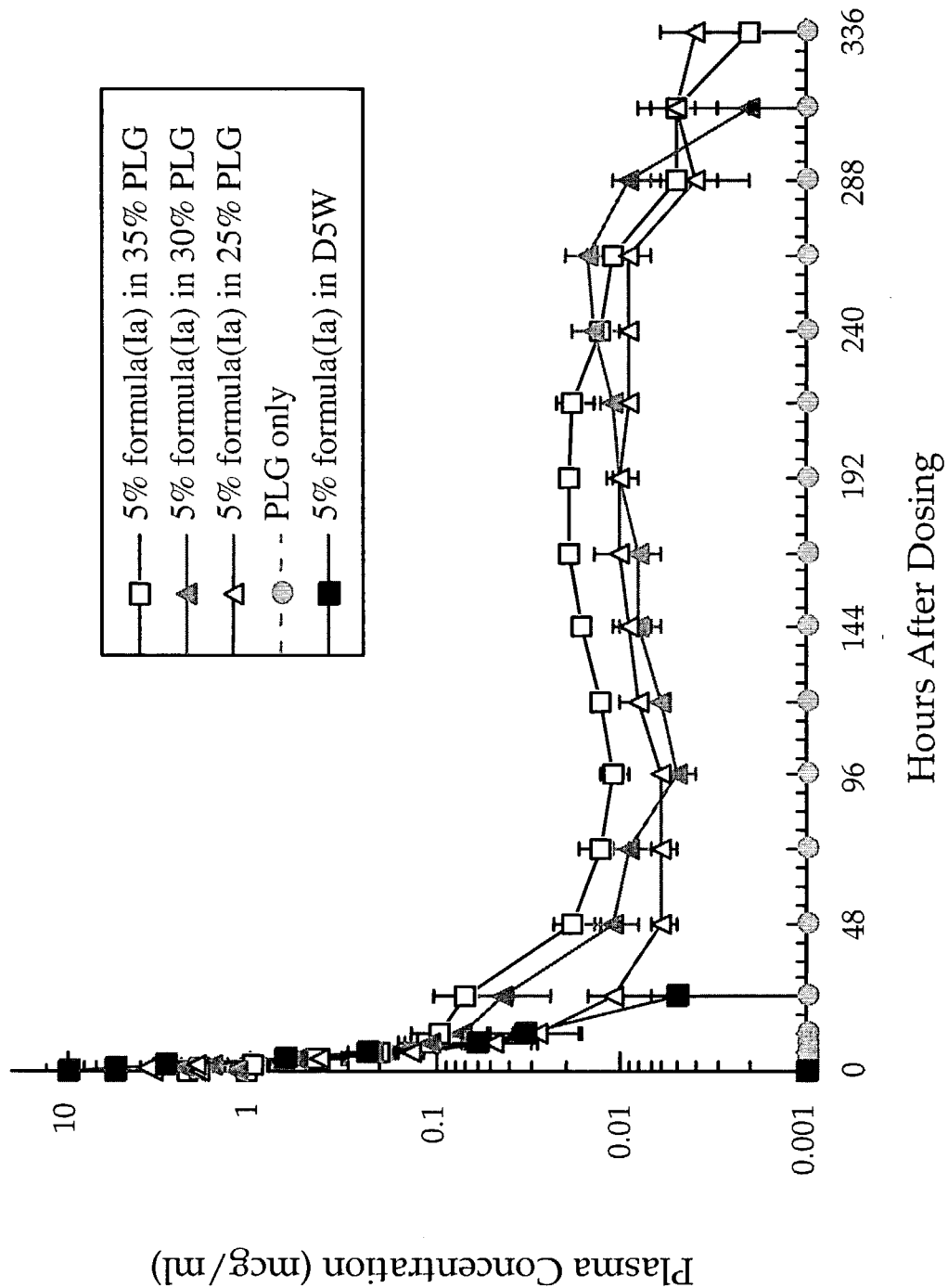
FIG. 2 illustrates the mean plasma concentrations of the compound of formula (Ia) in dogs following single subcutaneous injections of PLG (13 KD) gel formulations.

Concentrations of the acetate salt of formula (Ia) in plasma were determined by HPLC-MS. The results are summarized in FIG. 2. The acetate salt of formula (Ia) was rapidly absorbed from the injectable solution, with the peak concentration observed within one hour of dosing. A two-week sustained release of the compound of formula (Ia) was shown by all of the dogs injected with the gel formulations in 25-30% PLG and NMP/TA (2:1). Drug plasma concentrates were observable for all dogs up to 12 days after dosing and the concentrations were still detectable in ~50% of the dogs by day 14. In comparison, the group that was given the compound of formula (Ia) in D5W yielded drug plasma concentrations below the limits of quantitation within 24 hours after dosing.

EXAMPLE 6

Preparation of Formulations of the Compound of Formula (Ib) in PLG Gels (a) Formulation of 3% Acetate Salt of Formula (Ib) in 35% PLG and NMP/TA (1:1) (Formulation IV)

A 35% PLG solution in NMP/TA (1:1) was prepared by combining 8.140 g of TA, 8.132 g of NMP, and 8.761 g of PLG (13 KD, 50:50 polymer ratio). A portion of the mixture (4.414 g) was treated with of the acetate salt of formula (Ib) (prepared as described in Example 1c, 136.1 mg) and stirred with a magnetic stirring bar at room temperature until a homogeneous gel was formed. The resulting PLG gel (formulation IV) consisted of 2.99% acetate salt of formula (Ib), 33.95% PLG, 31.53% NMP and 31.53% TA (w/w) and could be stored under refrigeration.

(b) Formulation of 3% Acetate Salt of Formula (Ib) in 35% PLG and NMP/TA (2:1) (Formulation V)

A 35% PLG solution was prepared by combining 4.329 g of TA, 8.712 g of NMP, and 7.003 g of PLG (13 KD, 50:50 polymer ratio). A portion of the solution (4.844 g) was treated with 144.7 g of the acetate salt of formula (Ib) (prepared as described in Example 1c) and stirred at room temperature. The resulting PLG gel (formulation V) consisting of 2.90% acetate salt of formula (Ib), 33.93% PLG, 42.11% NMP and 21.06% TA (w/w) was stored under refrigeration.

EXAMPLE 7

In Vitro Drug Release of Acetate Salt of Formula (Ib) from PLG (13 KD) Gels

Figure 3:
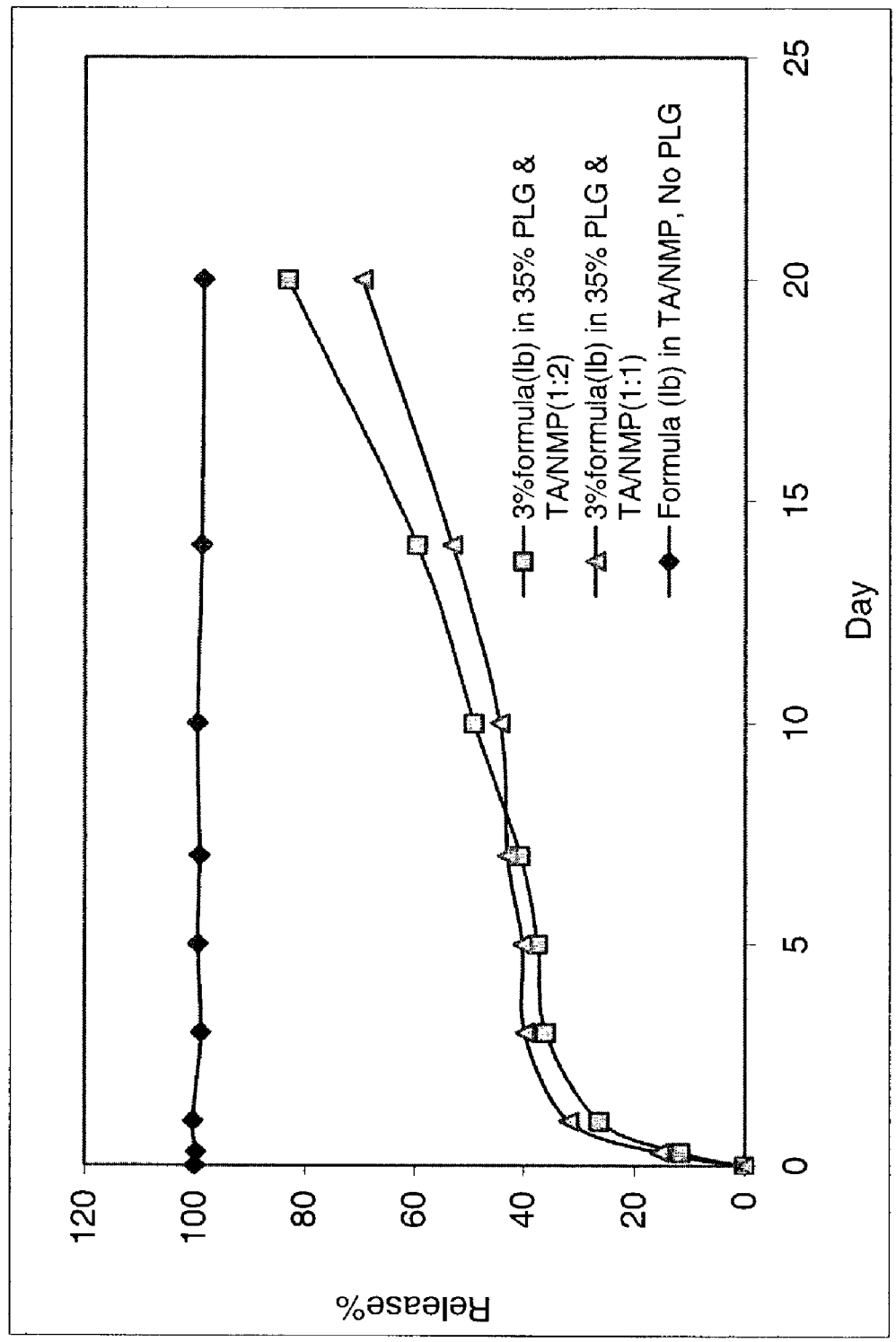
FIG. 3 illustrates the in vitro drug release profiles of the compound of formula (Ib) from PLG (13 KD) gel formulations at 37° C.

The in vitro drug release of the acetate salt of formula (Ib) from the PLG gel formulations (IV) and (V) (from Example 6) was determined by the method described in Example 4. As shown in FIG. 3, both formulations exhibited in vitro sustained release for two weeks, as opposed to the control, which showed no sustained release.

EXAMPLE 8

Pharmacokinetic Studies of Acetate Salt of Formula (Ib) in PLG Gels (a) Dog Study One in vivo pharmacokinetic study was done using dogs. Two groups of dogs were injected subcutaneously with the gel formulations IV and V (from Example 6), and a control group of dogs was injected with a solution of the compound of formula (Ib) in D5W. Each dog was administered with a dose of 30 mg of formulation. The drug release was determined by the measurement of the concentration of the compound of formula (Ib) in plasma using the same procedure as described in Example 5.

Figure 4:
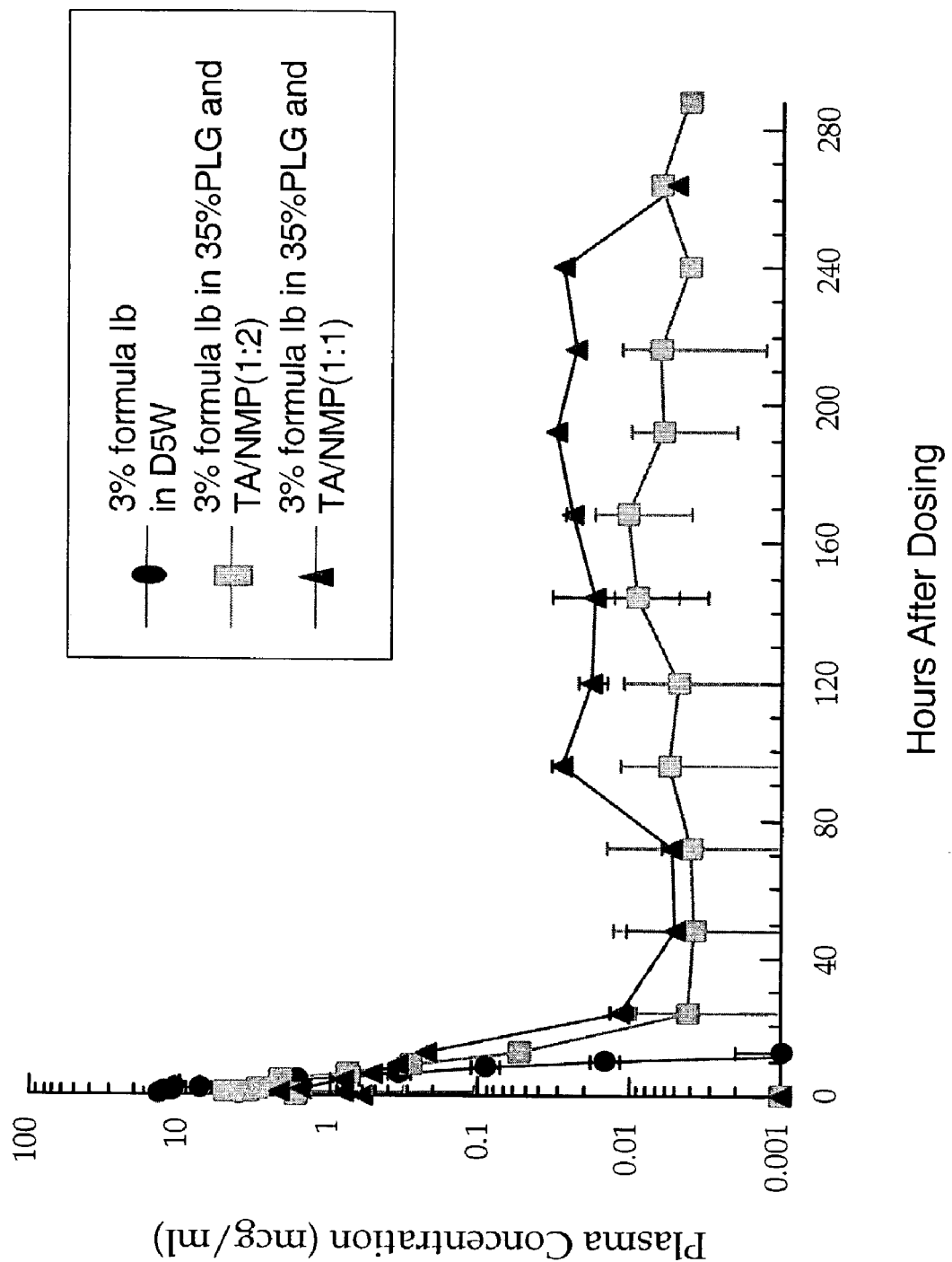
FIG. 4 illustrates the mean plasma concentrations of the compound of formula (Ib) in dogs following single subcutaneous injections of PLG (13 KD) gel formulations.

As shown in FIG. 4, sustained release was seen in all of the dogs injected with the formulations IV and V. All of the dogs dosed with formulations IV and V exhibited measurable drug plasma concentrations (above 10 ng/mL) up to 12 days after injection. In comparison, the group receiving the control in D5W yielded drug plasma concentrations below the limits of quantitation within 24 hours after dosing.

(b) Monkey Study

Figure 5:
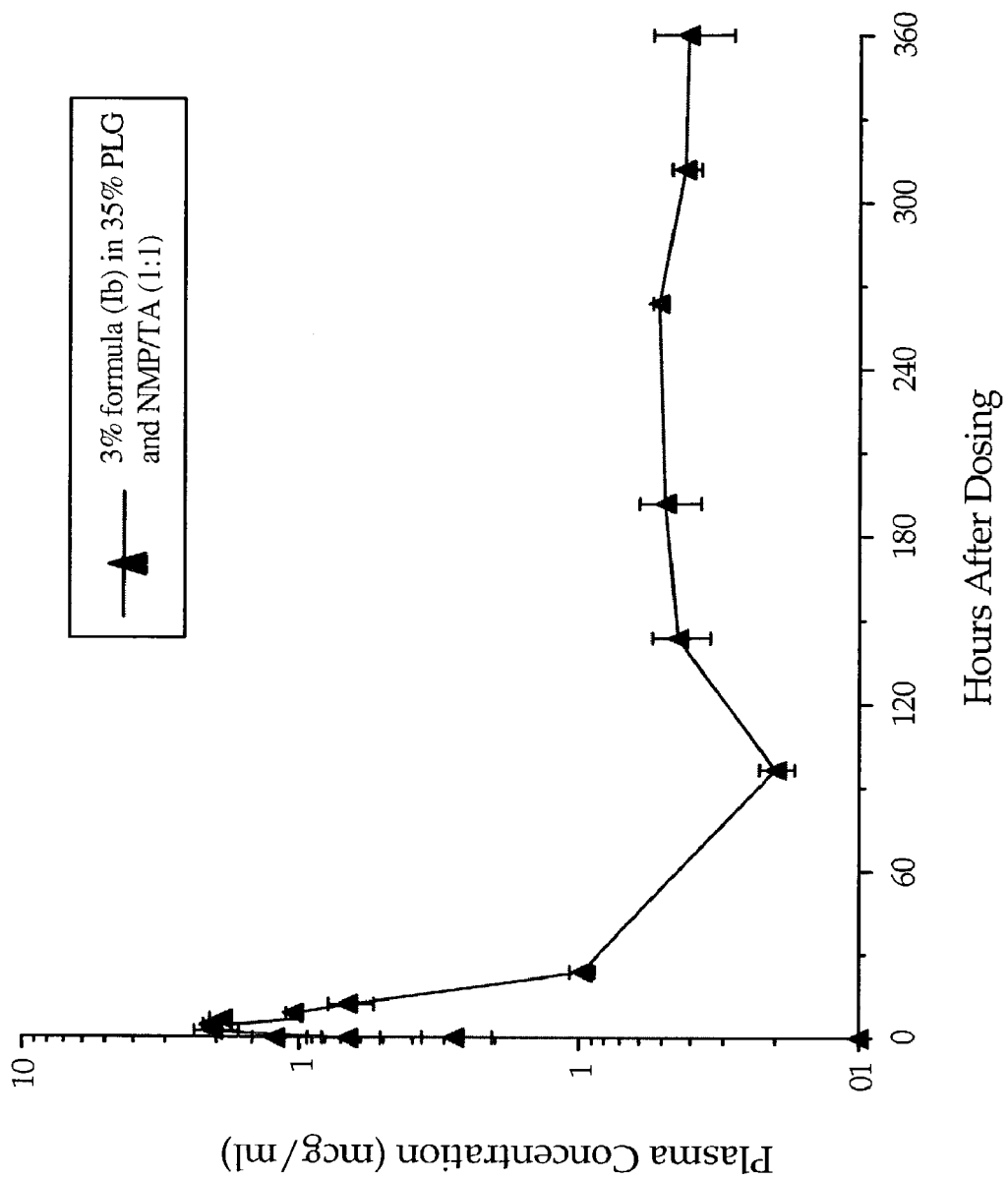
FIG. 5 illustrates the mean plasma concentrations of the compound of formula (Ib) in monkeys following single subcutaneous injections of PLG (13 KD) gel formulations.

Another in vivo pharmacokinetic study was performed using monkeys. Each monkey was injected subcutaneously with formulation IV (from Example 6) at a dose of 30 mg/monkey. Nine blood samples were obtained from the testing monkeys during the first 24 hours after dosing, with intermittent sampling for the following 15 days. The plasma concentrations of the compound of formula (Ib) were determined by HPLC-MS. As shown in FIG. 5, the release profile of formulation IV in monkeys was similar to that described in the dog study (a). A 15-day slow release of the compound of formula (Ib) from formulation IV was shown for all of the monkeys with the drug plasma concentrations in a range of about 40 ng/mL. In contrast, monkeys dosed with the compound of formula (I) in the absence of PLG had plasma concentrations that dropped to below detectable limits within one day.

EXAMPLE 9

In Vitro Drug Release of the Acetate Salt of Formula (Ia) from PLG (24 KD) Gels (a) Formulation of 3% Acetate Salt of Formula (Ia) in 35% PLG (24 KD) and NMP/TA (2:1)

The acetate salt of formula (Ia) (26.7 mg) (prepared as described in Example 1c) was added into a solution containing 0.3031 g of PLG (24 KD, 50:50 polymer ratio) and 0.571 g of NMP/TA (2:1). The mixture was stirred at room temperature and resulted in a viscous liquid formulation which consisted of 2.96% compound of formula (Ia), 33.65% PLG, 42.21% NMP and 21.18% TA (w/w).

(b) Formulation of 5% Acetate Salt of Formula (Ia) in 35% PLG (24 KD) and NMP/TA (4:1)

A solvent mixture of NMP/TA (4:1, w/w) was prepared from 4.012 g of NMP and 1.007 g of TA. A portion of the solvent mixture was treated with PLG (24 KD, 50:50 polymer ratio, 0.3001 g). The resulting 35% PLG gel solution in MP/TA (4:1) was further stirred with 44.7 mg of the acetate salt of formula (Ia) (prepared as described in Example 1c) at room temperature and became a viscous liquid which consisted of 4.92% acetate salt of formula (Ia), 33.15% PLG, 49.50% NMP and 12.43% TA (w/w).

EXAMPLE 10

In Vitro Drug Release of the Acetate Salt of Formula (Ia) from PLG (24 KD) Gels

Figure 6:
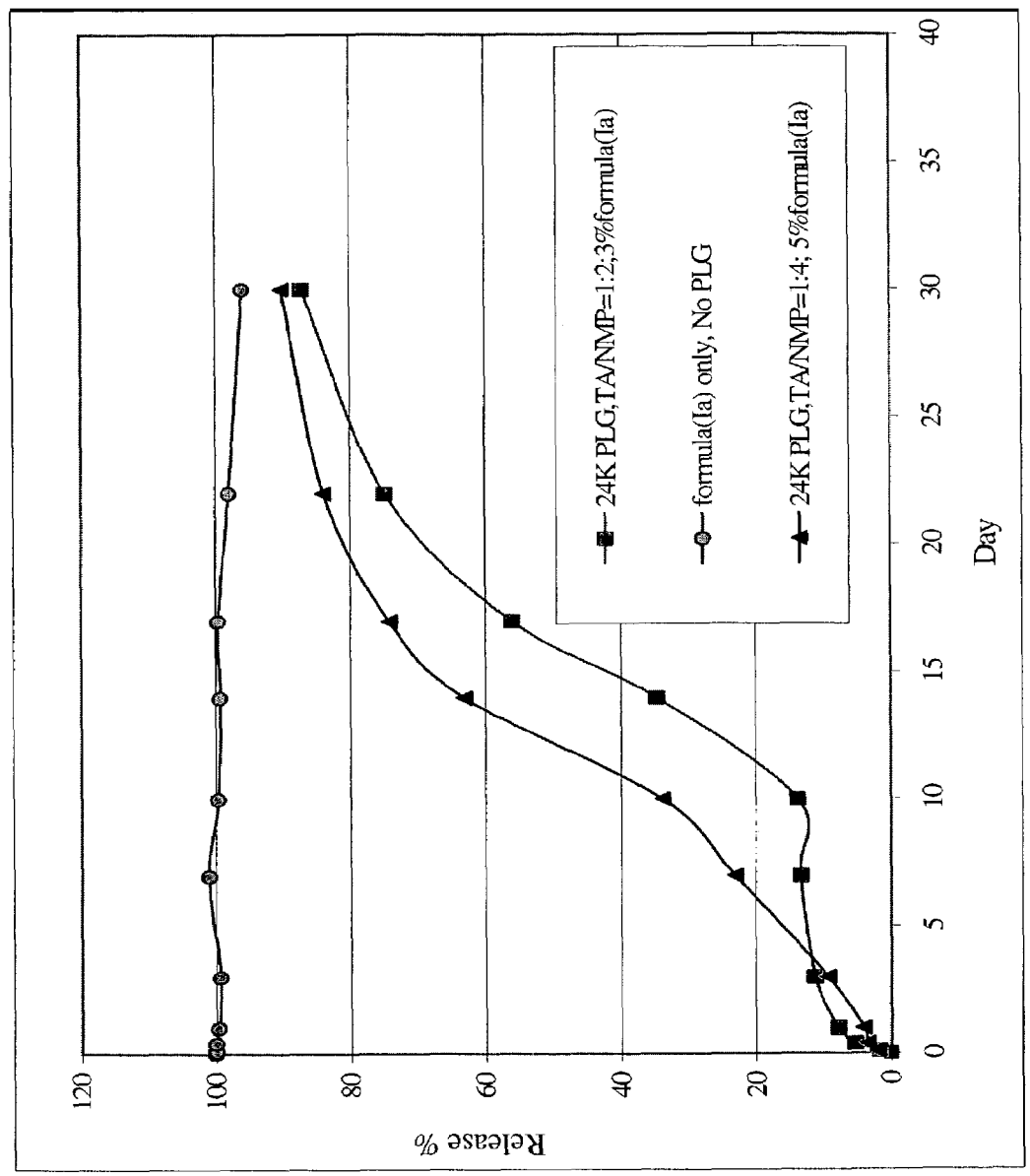
FIG. 6 illustrates the in vitro drug release profiles of the compound of formula (Ia) from PLG (24 KD) gel formulations at 37° C.

The in vitro drug release profiles of PLG (24 KD) gel formulations were obtained by the methods described in Example 4. As shown in FIG. 6, an increase of PLG molecular weight from 13 KD to 24 KD significantly prolonged the in vitro release of the acetate salt of formula (Ia) from the PLG gel, demonstrating sustained release for 30 days.

EXAMPLE 11

In Vitro Drug Release of Various Salts of Formula (Ib) from PLG (13 KD) Gels

Figure 7:
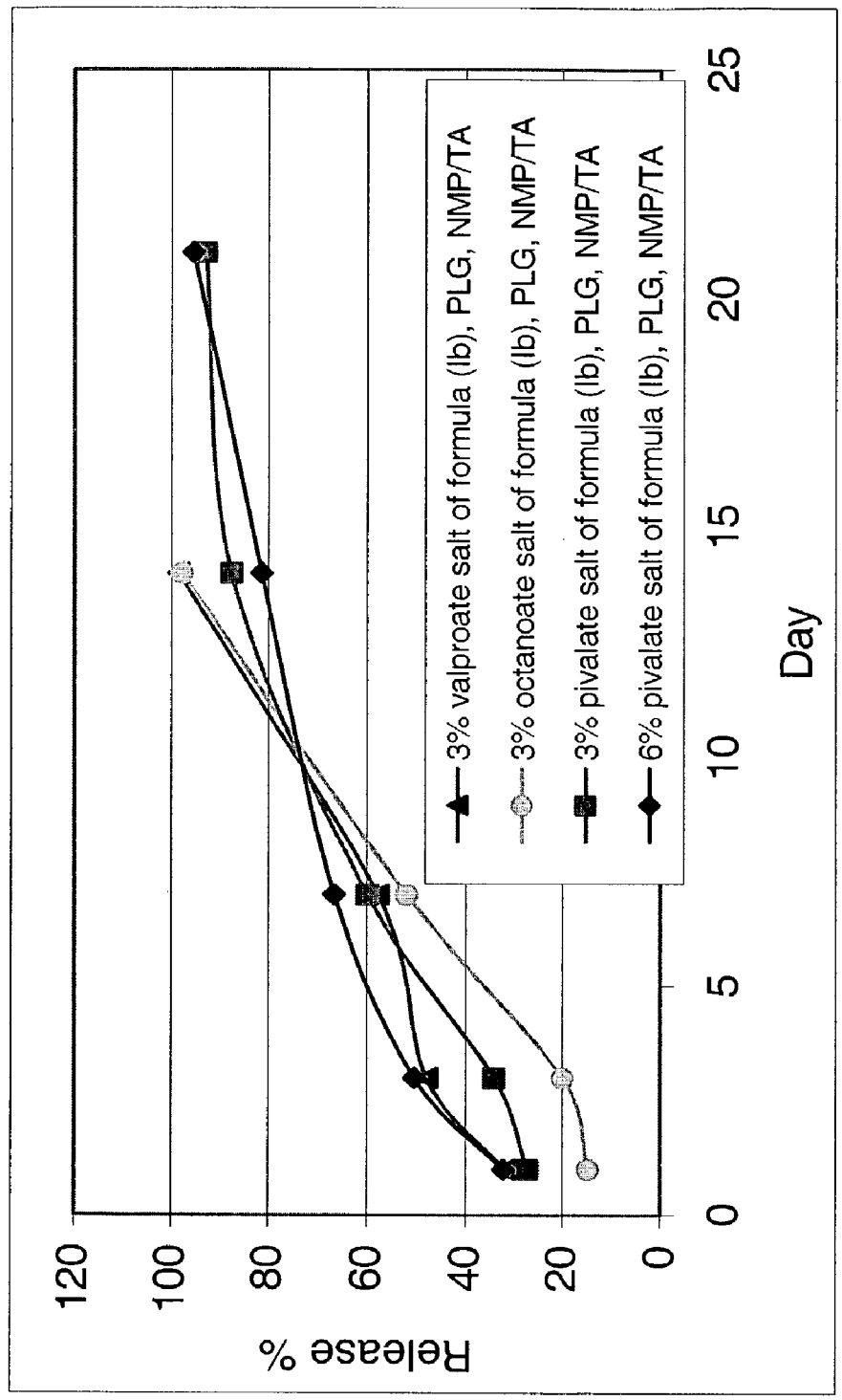
FIG. 7 illustrates the in vitro release profiles of the compound of formula (Ib) from PLG (13 KD) gel formulations at 37° C.

Formulations of valproate (formulation VI), octanoate (formulation VII), and pivalate (formulation VIII) salts of the compound of formula (Ib) were prepared by substituting the appropriate salts (prepared as described in Example 1b) for the acetate salt in Example 6B. Each PLG formulation contained 3.0% valproate, octanoate, or pivalate salt of formula (Ib), 33.9% PLG (13 KD, 50:50 polymer ratio), 42.1% NMP and 21.1% TA. In addition, a formulation (formulation IX) that contained 6.0% pivalate salt of formula (Ib), 32.9% PLG (13 KD, 50:50 polymer ratio), 40.4% NMP and 20.7% TA was also prepared. The in vitro drug release profiles of formulations VI, VII, VIII, and IX were obtained by the methods described in Example 4 substituting 50 mM phosphate buffer (pH 7.4) for 5 mM PBS buffer. As shown in FIG. 7, the in vitro release profiles of the pivalate salt of formula (Ib) from formulations VIII and IX exhibited sustained release for 21 days. The in vitro release profiles of the valproate and octanoate salts of the compound of formula (Ib) from formulations VI and VII demonstrated sustained release for 14 days.

EXAMPLE 12

Pharmacokinetic Study of Pivalate Salt of Formula (Ib) in PLG Gels

An in vivo pharmacokinetic study of the pivalate salt of the compound of formula (Ib) in PLG gel was conducted in dogs. Three dogs were injected subcutaneously with formulation IX from Example 11. Each of the formulations was administered at a dose of 60 mg/dog. The drug release was determined by the measurement of the concentration of the pivalate salt of formula (Ib) in plasma using the same procedure as described in Example 4.

Figure 8:
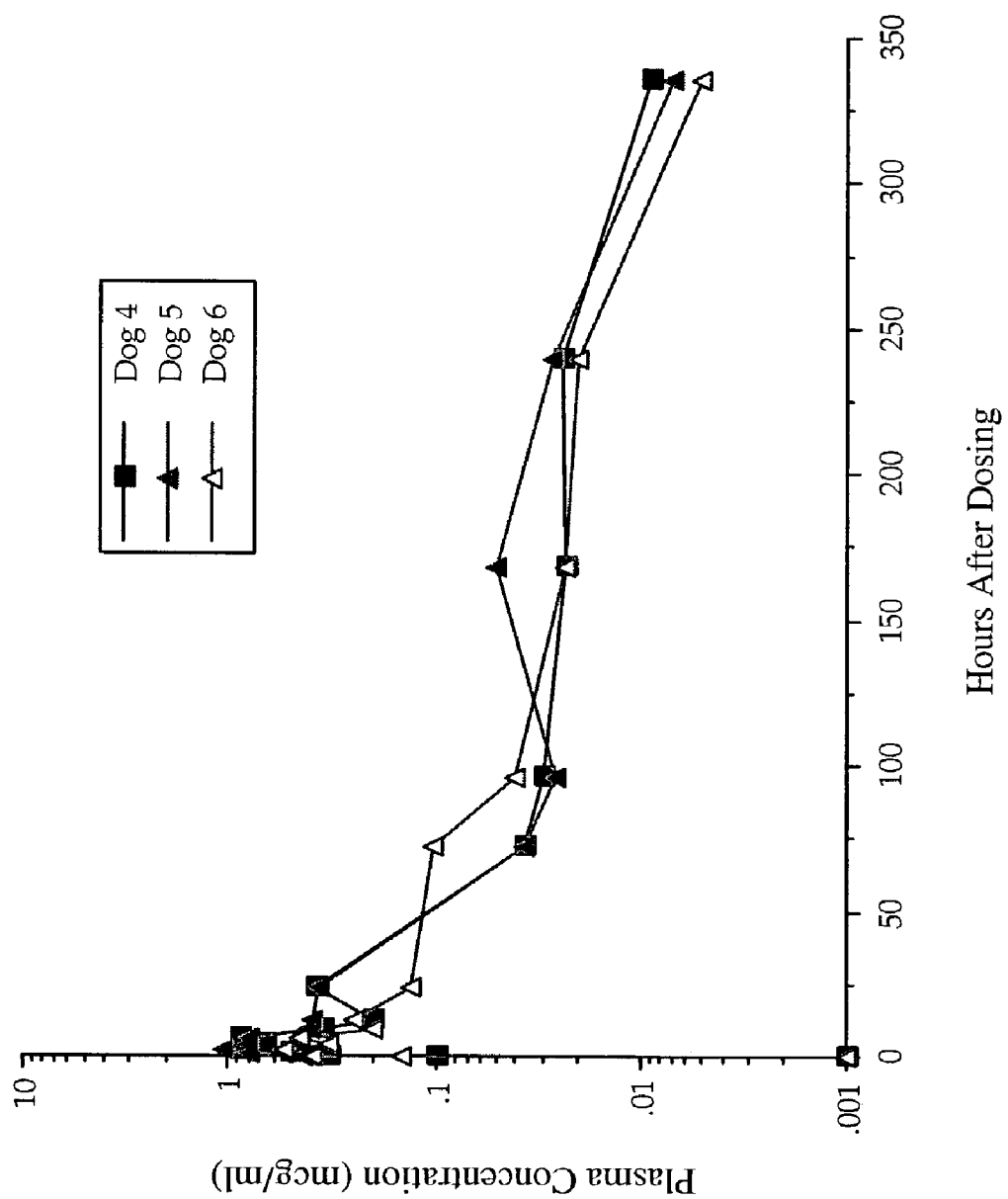
FIG. 8 illustrates the mean plasma concentrations of the compound of formula (Ib) in dogs following single subcutaneous injections of PLG (13 KD) gel formulations.

As shown in FIG. 8, sustained release was seen in all of the dogs injected with formulation IX. All three dogs exhibited measurable drug plasma concentrations (above 7 ng/mL) up to 14 days after injection.

EXAMPLE 13

Figure 9:
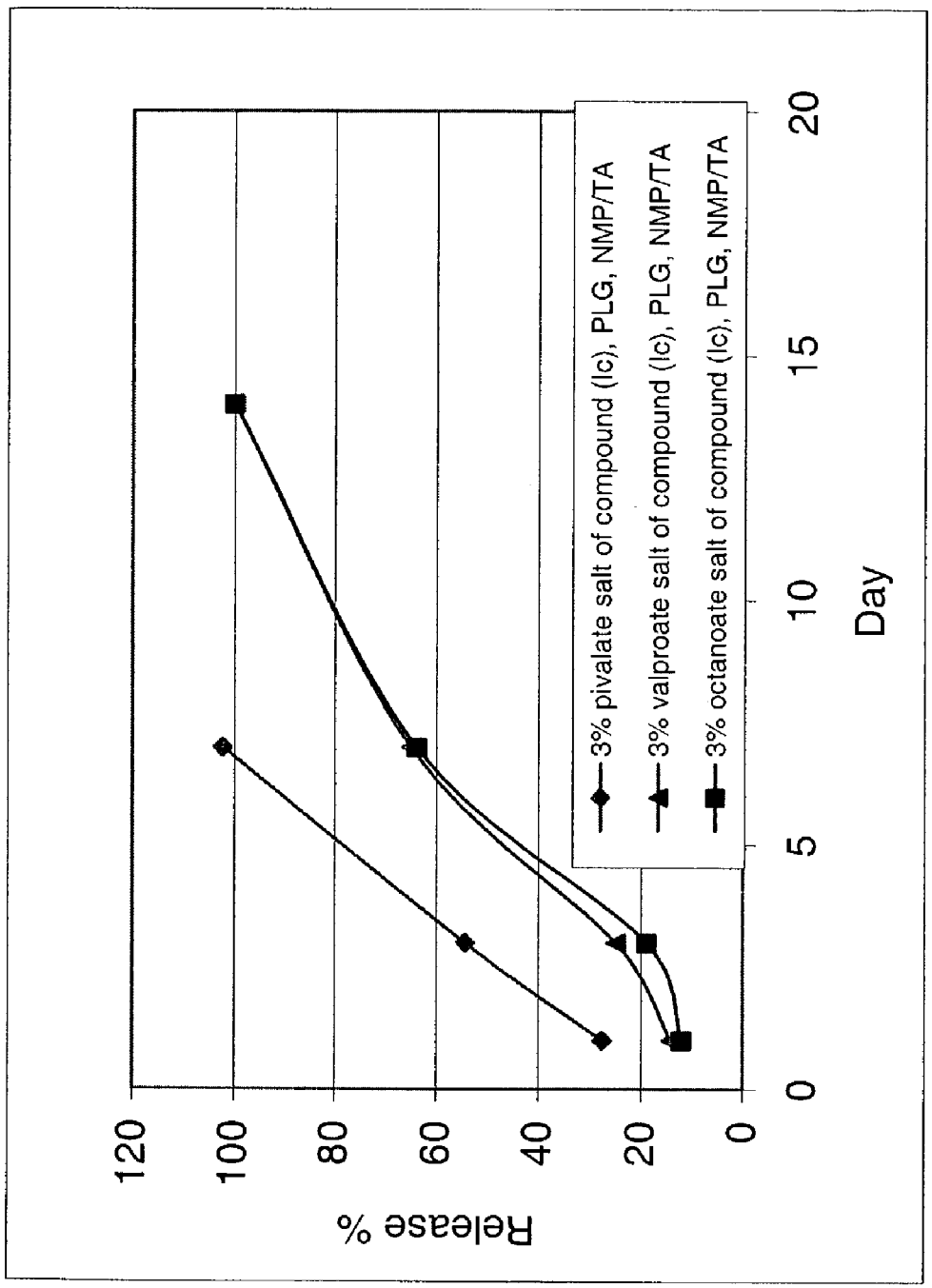
FIG. 9 illustrates the in vitro release profiles of the compound of formula (Ic) from PLG (13 KD) gel formulations at 37° C.

In Vitro Drug Release of Various Salts the Compound of Formula (Ic) from PLG Gel Formulations of valproate (formulation X), octanoate (formulation XI), and pivalate (formulation XII) salts of the compound of formula (Ic) were prepared by substituting the appropriate salts (prepared as described in Example 1b) for the acetate salt in Example 6B. Each PLG formulation contained 3.0% pivalate, valproate, or octanoate salt of formula (Ic), 33.9% PLG (13 KD, 50:50 polymer ratio), 42.1% NMP and 21.1% TA. The in vitro drug release profiles of formulations X, XI, and XII were obtained by the method described in Example 3 substituting 50 mM phosphate buffer (pH 7.4) for 5 mM PBS buffer. As shown in FIG. 9, the in vitro release of the pivalate salt of formula (Ic) from formulation X demonstrated sustained release for 7 days. The in vitro release of the valproate and octanoate salts of formula (Ic) from formulations XI and XII exhibited sustained release for 14 days.

EXAMPLE 14

Pharmacokinetic Study of Acetate Salt of Formula (Ic) in PLG Gel

A PLG formulation (formulation XIII) containing 3.0% acetate salt of formula (Ic) (prepared as described in Example 1c), 33.9% PLG (13 KD, 50:50 polymer ratio), 42.1% NMP and 21.1% TA was prepared by the method as described in Example 6B. An in vivo pharmacokinetic study of formulation XIII was conducted in a group of three dogs. Each dog was injected subcutaneously with a dose of 30 mg of formulation XIII. The drug release was determined by the measurement of the concentration of the acetate salt of formula (Ib) in plasma using the method described in Example 5.

Figure 10:
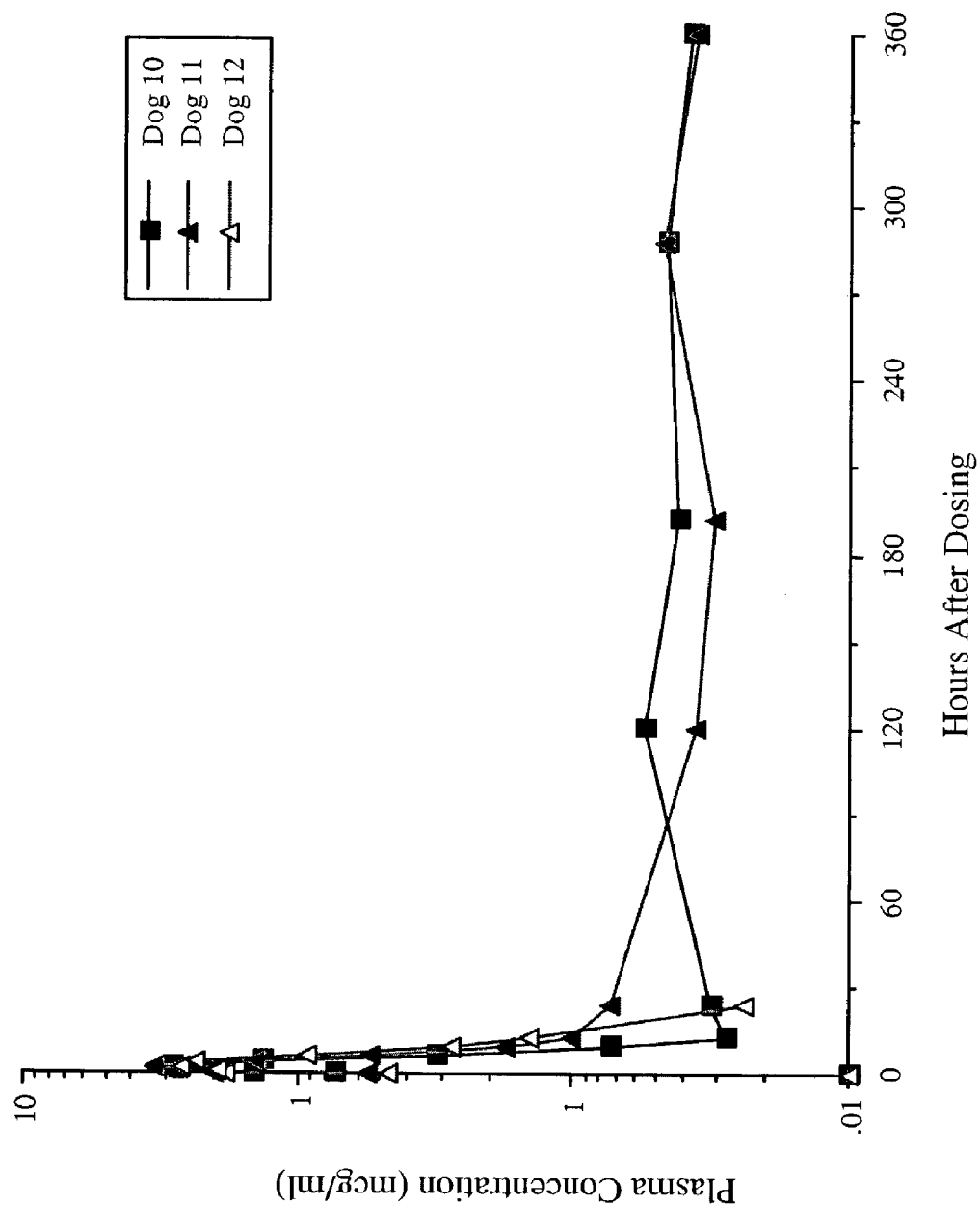
FIG. 10 illustrates the mean plasma concentrations of the compound of formula (Ic) in dogs following single subcutaneous injections of PLG (13 KD) gel formulations.

FIG. 10 shows a drug plasma concentration-time profile for formulation XIII. Two of three dogs exhibited measurable drug plasma concentrations (above 25 ng/mL) up to 14 days after injection. One dog exhibited measurable drug plasma concentrations up to 24 hours after injection.

EXAMPLE 15

Figure 11:
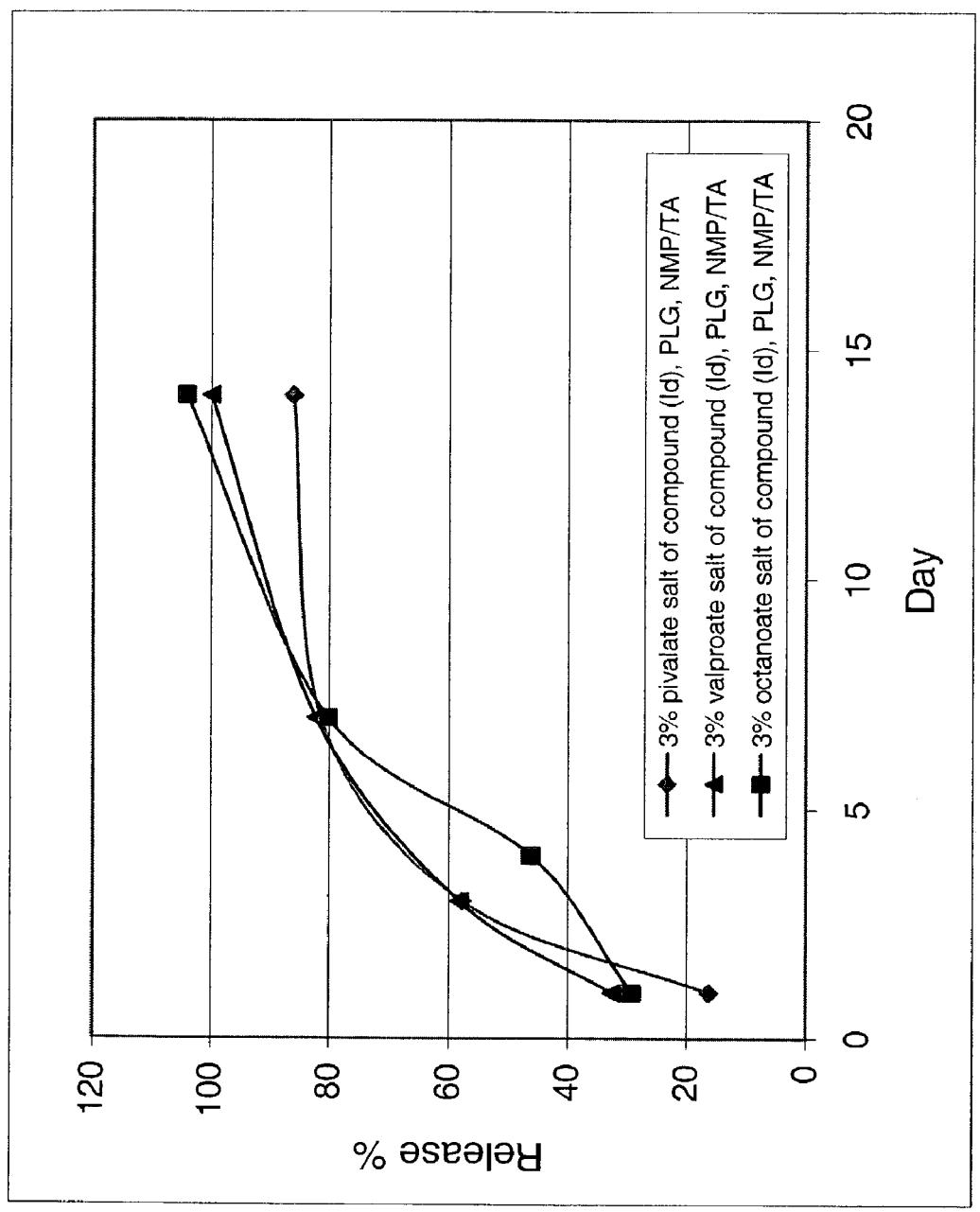
FIG. 11 illustrates the in vitro release profiles of the compound of formula (Id) from PLG (13 KD) gel formulations at 37° C.

In Vitro Drug Release of Various Salt of the Compound of Formula (Id) from PLG Gel Formulations of valproate (formulation XIV), octanoate (formulation XV), and pivalate (formulation XVI) salts of the compound of formula (Id) were prepared by substituting the appropriate salts (prepared as described in Example 1b) for the acetate salt in Example 6B. Each PLG formulation contained 3.0% pivalate, valproate, or octanoate salt of the compound of formula (Id), 33.9% PLG (13 KD, 50:50 polymer ratio), 42.1% NMP and 21.1% TA. The in vitro drug release profiles of formulations XIV, XV, and XVI were obtained by the method described in Example 4 substituting 50 mM phosphate buffer (pH 7.4) for 5 mM PBS buffer. As shown in FIG. 11, the in vitro release profiles of all three salts of formula (Id) demonstrated sustained release for 14 days.

Using the procedures described in PCT/US02/34811, and PCT/US02/34760 and the preceding examples, PLG gel formulations can also be prepared for the following peptides:

N-Ac-DalloIle-Thr-Ser-Ile-Arg-ProNHCH$_2$CH$_3$;
N-Ac-Thr-Gln-Ile-Arg-ProNHCH$_2$CH$_3$ (SEQ ID NO:2); and
N-Ac-Gly-Gln-DIle-Thr-Nva-Ile-Arg-Pro-DAlaNH$_2$.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

---

What is claimed is:

1. A pharmaceutical composition comprising:
   (a) N-Ac-Gly-Val-D-alloIle-Ser-Gln-Ile-Arg-ProNHCH$_2$CH$_3$ or a pharmaceutically acceptable salt thereof;
   (b) poly(lactide-co-glycolide); and
   (c) an organic solvent.

2. The pharmaceutical composition of claim 1 wherein the pharmaceutically acceptable salt is selected from the group consisting of acetate, pivalate, valproate, and octanoate.

3. The pharmaceutical composition of claim 1 which comprises between about 1% and about 15% (w/w) of N-Ac-Gly-Val-D-alloIle-Ser-Gln-Ile-Arg-ProNHCH$_2$CH$_3$ or a pharmaceutically acceptable salt thereof.

4. The pharmaceutical composition of claim 1 which comprises between about 3% and about 6% (w/w) of N-Ac-Gly-Val-D-alloIle-Ser-Gln-Ile-Arg-ProNHCH$_2$CH$_3$ or a pharmaceutically acceptable salt thereof.

5. The pharmaceutical composition of claim 1 which comprises between about 25% and about 45% (w/w) poly(lactide-co-glycolide).

6. The pharmaceutical composition of claim 5 which comprises about 35% (w/w) poly(lactide-co-glycolide).

7. The pharmaceutical composition of claim 1 wherein the poly(lactide-co-glycolide) has a weight of between about 6 and about 60 KD.

8. The pharmaceutical composition of claim 7 wherein the poly(lactide-co-glycolide) has a weight of between about 13 and about 24 KD.

9. The pharmaceutical composition of claim 1 wherein the organic solvent is N-methyl-2-pyrrolidinone.

10. The pharmaceutical composition of claim 1 wherein the organic solvent is triacetin.

11. The pharmaceutical composition of claim 1 wherein the organic solvent is a mixture of N-methyl-2-pyrrolidinone and triacetin.

12. The pharmaceutical composition of claim 11 wherein the N-methyl-2-pyrrolidinone and the triacetin are in a weight ratio of from about 1:2 to about 6:1.

13. The pharmaceutical composition of claim 11 wherein the N-methyl-2-pyrrolidinone and the triacetin are in a weight ratio of about 2:1.

14. The pharmaceutical composition of claim 11 wherein the N-methyl-2-pyrrolidinone and the triacetin are in a weight ratio of about 1:1.

15. A pharmaceutical composition comprising:
    (a) about 3% (w/w) of N-Ac-Gly-Val-D-alloIle-Ser-Gln-Ile-Aw-ProNHCH$_2$CH$_3$ (formula Id), or a pharmaceutically acceptable salt thereof;
    (b) about 34% (w/w) poly(lactide-co-glycolide); and
    (c) about a 2:1 (w/w) mixture of N-methylpyrrolidinone and triacetin.

16. The pharmaceutical composition of claim 15 wherein the therapeutically acceptable salt is selected from the group consisting of acetate, pivalate, valproate, and octanoate.

* * * * *

UNITED STATES PATENT AND TRADEMARK OFFICE
CERTIFICATE OF CORRECTION

PATENT NO. : 7,432,245 B2
APPLICATION NO. : 10/456831
DATED : October 7, 2008
INVENTOR(S) : Haviv et al.

It is certified that error appears in the above-identified patent and that said Letters Patent is hereby corrected as shown below:

Column 18, line 55, in claim 15, delete "Aw" and insert -- Arg --.

Signed and Sealed this

Twenty-second Day of June, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = is absent or sacrosyl at position 1
<220> FEATURE:
<221> NAME/KEY: VARIANT
<222> LOCATION: (2)...(2)
<223> OTHER INFORMATION: Xaa = is absent or glycyl at position 2
<220> FEATURE:
<221> NAME/KEY: VARIANT
<222> LOCATION: (3)...(3)
<223> OTHER INFORMATION: Xaa = is absent or selected from the group
      consisting of glutaminyl and valyl at position 3
<220> FEATURE:
<221> NAME/KEY: VARIANT
<222> LOCATION: (4)...(4)
<223> OTHER INFORMATION: Xaa = is absent or selected form the group
      consisting of D-alloisoleucyl and D-isoleucyl at
      position 4
<220> FEATURE:
<221> NAME/KEY: VARIANT
```

```
<222> LOCATION: (5)...(5)
<223> OTHER INFORMATION: Xaa = is selected from the group consisting of
      seryl and threonyl at position 5
<220> FEATURE:
<221> NAME/KEY: VARIANT
<222> LOCATION: (6)...(6)
<223> OTHER INFORMATION: Xaa = is selected from the group consisting of
      glutaminyl, norvalyl and seryl at position 6
<220> FEATURE:
<221> NAME/KEY: VARIANT
<222> LOCATION: (10)...(10)
<223> OTHER INFORMATION: Xaa = is selected from the group consisting of
      -NHCH2CH3 and D-alanylethylamide; provided that
      when Xaa4 is D-alloisoleucyl, Xaa1 is absent at
      position 10

<400> SEQUENCE: 1

Xaa Xaa Xaa Xaa Xaa Xaa Ile Arg Pro Xaa
 1               5                   10

<210> SEQ ID NO 2
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = ProNHCH2CH3 or prolyl-N-ethylamide at
      position 5

<400> SEQUENCE: 2

Thr Gln Ile Arg Xaa
 1               5
```